United States Patent [19]
Mori et al.

[11] Patent Number: 4,780,145
[45] Date of Patent: Oct. 25, 1988

[54] GEL COMPOSITION COMPRISING CYCLIC DIMETHYL POLYSILOXANES

[75] Inventors: Shigeru Mori; Satoshi Kuwata, both of Annaka, Japan

[73] Assignee: Shin-Etsu Chemical Co., Ltd., Tokyo, Japan

[21] Appl. No.: 139,091

[22] Filed: Dec. 22, 1987

[30] Foreign Application Priority Data

Dec. 23, 1986 [JP] Japan ................ 61-310534

[51] Int. Cl.$^4$ .................... C08L 5/02; C09D 3/22
[52] U.S. Cl. .................... 106/206; 106/208; 106/211
[58] Field of Search ............ 106/206, 208, 211

[56] References Cited

U.S. PATENT DOCUMENTS

| 2,156,488 | 8/1937 | Bode | 106/206 |
| 2,800,458 | 7/1957 | Green | 106/206 |
| 2,856,307 | 10/1958 | Fredrickson | 106/208 |
| 2,993,872 | 7/1961 | Gagnon et al. | 106/211 |
| 4,318,746 | 3/1982 | Claffey et al. | 106/206 |
| 4,626,288 | 12/1986 | Trzasko et al. | 106/211 |

Primary Examiner—Paul Lieberman
Assistant Examiner—Willie J. Thompson
Attorney, Agent, or Firm—Lowe, Price, LeBlanc, Becker & Shur

[57] ABSTRACT

A gel composition which comprises a specific type of cyclic dimethyl polysiloxane, an animal or plant oil or vaseline, and an ester of dextrin with a fatty acid having from 8 to 20 carbon atoms. The cyclic dimethyl polysiloxane is methyl-substituted cyclotetrasiloxane, cyclopentasiloxane or cyclohexasiloxane. The use of this type of cyclosiloxane contributes to impart good spreadability on the skin to the composition.

9 Claims, No Drawings

GEL COMPOSITION COMPRISING CYCLIC DIMETHYL POLYSILOXANES

BACKGROUND OF THE INVENTION

1. Field of the Invention

This invention relates to cosmetic or medical articles and more particularly, to gel compositions which are useful in application to cosmetic or medical pastes or creams and are comprised of cyclic dimethyl polysiloxanes.

2. Description of the Prior Art

It is well known that various types of silicone oils are added to cosmetic or medical pastes or creams. These silicone oils are merely used as additives, not as a base for the pastes or creams. This is because gelation of silicone oils requires addition of hydrophobic silica or bentonite as an inorganic filler or thickener. In addition, the silicone oil used should have a relatively high viscosity of not less than 100 centistokes at 25° C. When this type of gel product is applied onto a skin surface, good spreadability is not obtained. Since little volatile matter is contained in the gel product, stickiness is undesirably left on the skin insofar as the gel is not removed therefrom. Accordingly, there is a demand for a gel composition which can be used as a base of pastes or creams without involving the disadvantages in the known counterparts.

SUMMARY OF THE INVENTION

It is an object of the invention to provide a silicone gel composition which meets the above demand.

It is another object of the invention to provide a gel composition which exhibits good spreadability on the skin surface and is rarely sticky to the touch.

It is a further object of the invention to provide a gel composition which is harmless and can be used as a base of medical or cosmetic pastes or creams.

The above objects can be achieved, according to the invention, by a gel composition which comprises:

(A) from 90 to 30 parts by weight of a cyclic dimethyl polysiloxane of the following general formula

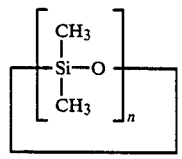

wherein n is an integer of from 4 to 6;

(B) from 5 to 50 parts by weight of at least one member selected from the group consisting of animal and plant oils and vaseline; and (C) from 5 to 30 parts by weight of an ester of dextrin and a fatty acid having from 8 to 20 carbon atoms provided that at least one R per glucose unit is an acyl group and m is an integer of from 20 to 40, the total amount of the ingredients (A), (B) and (C) being 100 parts by weight.

As will be apparent from the above, the present invention is characterized in that a cyclic dimethyl polysiloxane having a low degree of polymerization is used as a base of the silicone gel composition of the invention. This gel composition is readily obtained by mixing the polysiloxane with one or more of animal and plant oils and vaseline products and also with an ester of dextrin and a fatty acid.

DETAILED DESCRIPTION OF THE INVENTION

The cyclic dimethyl polysiloxane used as one ingredient of the gel composition of the invention is represented by the following general formula

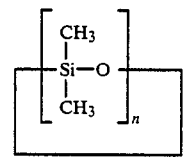

in which n is an integer of from 4 to 6. Specific examples of the polysiloxane include octamethylcyclotetrasiloxane having a boiling point of 175° C. and a viscosity of 2.3 centistokes at 25° C., decamethylcyclopentasiloxane having a boiling point of 210° C. and a viscosity of 3.9 centistokes at 25° C., and dodecamethylcyclohexasiloxane having a boiling point of 245° C. and a viscosity of 6.6 centistokes at 25° C. These compounds may be used singly or in combination. If the amount of the polysiloxane is less than 30 parts by weight per 100 parts by weight of the composition, the other ingredients are correspondingly increased in amount, so that good spreadability as will be expected in the composition of the invention cannot be realized with an increasing degree of stickiness. Over 90 parts by weight, it becomes difficult to satisfactorily gel the composition. Accordingly, the amount of the polysiloxane compound is generally in the range of from 90 to 30 parts by weight, preferably from 85 to 40 parts by weight, per 100 parts by weight of the gel composition.

The ingredient (B) of the composition should be an oily substance selected from plant and animal oils, vaseline, and mixtures thereof. The plant and animal oils may be any known plant and animal oils and fats. Typical examples of the oils include jojoba oil, soybean oil, peanut oil, wheat germ oil, olive oil, rose oil, cotton seed oil, camellia oil, rubber seed oil, coconut oil, Saint John's wort oil, clove oil, terpentine oil, safflower oil, rice bran oil, palm oil, macademia oil, bees wax, lanolin, whale oil, tallow, lard, and the like. These oils or fats and vaseline may be used singly or in combination. The amount of the oils or vaseline is in the range of from 5 to 50 parts by weight per 100 parts by weight of the composition. If the amount is less than 5 parts by weight, the composition is unlikely to gel. Over 50 parts by weight, good spreadability of the gel composition cannot be expected with an increasing degree of stickiness to the touch. Preferably, the amount ranges from 7 to 45 parts by weight in 100 parts by weight of the composition.

The ingredient (C) used in the present invention is an ester of dextrin and a fatty acid. The the ester may be represented by the following formula

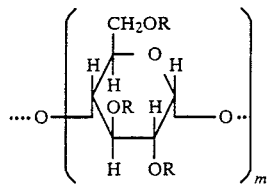

in which each R represents a hydrogen atom or an acyl group having from 8 to 20 carbon atoms provided that at least one R per glucose unit is an acyl group, and m is an integer of from 20 to 30. As will be apparent from the above definition, the ester may be a partial ester. The fatty acids useful in the practice of the invention may be saturated or unsaturated acids and include, for example, capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachic acid, oleic acid, linoleic acid, linolenic acid, and the like. These dextrin and fatty acid esters may be available, for example, under the designation of Rheopearl series from Chiba Seifun Co., Ltd. of Japan.

The amount of the (C) ingredient is generally in the range of from 5 to 30 parts by weight, preferably from 7 to 25 parts by weight, per 100 parts by weight of the composition. This is because when the amount is less than 5 parts by weight, the composition is unlikely to gel, whereas over 30 parts by weight, the resultant composition becomes too hard or semi-solid, resulting in poor spreadability or covering capacity.

The gel composition of the invention can be readily obtained by mixing predetermined amounts of the ingredients (A), (B) and (C) and heating the mixture to a temperature of, for example, from 60° to 70° C. to obtain a uniform solution, and quenching the solution. As a matter of course, the gel composition may further comprise various types of oils, antioxidants, pigments, dyes, perfumes or the like additives, if desired.

The gel composition of the invention exhibits good spreadability on the skin. The cyclic dimethyl polysiloxane used as the main ingredient (A) is so volatile and low in viscosity that it readily evaporates off. This is advantageous in that after application of the gel composition, wetting to the touch is not left over a long term. Thus, the gel composition is considered to be useful especially as a base for cosmetics or medical articles.

The present invention is described in more detail by way of examples in which parts are by weight and gel characteristics are those determined according to the method prescribed in JIS K2220.

EXAMPLES 1-10

Decamethylcyclopentasiloxane (KF995 available from Shinetsu Chemical Ind. Co., Ltd.) or octamethylcyclotetrasiloxane (KF994 available from Shinetsu Chemical Ind. Co., Ltd.), plant and animal oils or vaseline indicated in the table, and a dextrin fatty acid ester (Rheopearl KL available from Chiba Seifun Co., Ltd.) were charged at ratios indicated in the Table into a 2,500 ml glass flask. Thereafter, the respective mixture were agitated at a temperature of 60° to 70° C. to obtain a uniform solution, whereupon the agitation was stopped, and the solution was subsequently quenched on an iced water bath to obtain a uniform gel composition. The gel composition was subjected to measurement of gel charcteristics, i.e. consistency and oil separation. The results are shown in the table. From the table, it will be seen that final hardnesses of the gel compositions are different from one another and some may be resistant in application to the skin, but all the compositions spread well on the skin with a reduced degree of stickiness.

TABLE

| | Composition | | | | | Gel Characteristics | |
|---|---|---|---|---|---|---|---|
| | Ingredient (A) | | Ingredient (B) | | Ingredient (C) Rheopearl KL | | Oil Separation (%) |
| Example No.: | | Amount (parts) | | Amount (parts) | Amount (parts) | Consistency | 40° C. × 24 hrs. |
| 1 | KF995 | 70 | jojoba oil | 15 | 15 | 261 | 0.7 |
| 2 | " | 48 | jojoba oil | 45 | 7 | 380 | 5.8 |
| 3 | KF994 | 68 | jojoba oil | 7 | 25 | 152 | below 0.1 |
| 4 | " | 40 | soybean oil | 40 | 20 | 196 | " |
| 5 | KF995 | 70 | bees wax | 17 | 13 | 157 | " |
| 6 | " | 70 | vaseline | 17 | 13 | 242 | 4.5 |
| 7 | " | 85 | camellia oil | 8 | 7 | 388 | 7.1 |
| 8 | KF994 | 70 | peanut oil | 15 | 15 | 270 | 2.2 |
| 9 | " | 72 | olive oil | 16 | 12 | 241 | 4.2 |
| 10 | " | 68 | rose oil | 19 | 13 | 278 | 3.9 |

COMPARATIVE EXAMPLE 270 g of cyclic dimethyl polysiloxane KF994 used in the above examples were mixed with 30 g of Rheopearl KL and agiated in a 500 ml glass flask at 60° to 70° C. As a result, it was found that the Rheopearl KL did not dissolve uniformly. After the agitation, the mixture was quenched on an iced water bath, whereupon the Rheopearl KL settled and no gelation took place.

When the above procedure was repeated using cyclic dimethyl polysiloxane KF995 was used, Rheopearl KL did not dissolve uniformly and no gelation took place when the mixture was quenched.

What is claimed is:

1. A gel composition which comprises the following ingredients (A), (B) and (C):

(A) from 90 to 30 parts by weight of a cyclic dimethyl polysiloxane of the following general formula

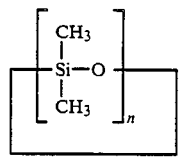

wherein n is an integer of from 4 to 6;

(B) from 5 to 50 parts by weight of at least one member selected from the group consisting of animal and plant oils and vaseline; and (C) from 5 to 30 parts by weight of an ester of dextrin and a fatty acid of the following general formula

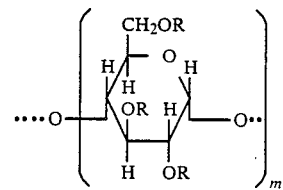

in which each R represents a hydrogen atom or an acyl group having from 8 to 20 carbon atoms provided that at least one R per glucose unit is an acyl group, and m is an integer of from 20 to 30, the total amount of the ingredients (A), (B) and (C) in the composition being 100 parts by weight.

2. A gel composition according to claim 1, wherein the ingredient (A) is octamethylcyclotetrasiloxane.

3. A gel composition according to claim 1, wherein the ingredient (A) is decamethylcyclopentasiloxane.

4. A gel composition according to claim 1, wherein the ingredient (A) is dodecamethylcyclohexasiloxane.

5. A gel composition according to claim 1, wherein the ingredient (A) is a mixture of at least two of octamethylcyclotetrasiloxane, decamethylcyclopentasiloxane and dodecamethylcyclohexasiloxane.

6. A gel composition according to claim 1, wherein the ingredient (A) is used in an amount of from 85 to 40 parts by weight per 100 parts of the composition.

7. A gel composition according to claim 1, wherein the ingredient (B) is used in an amount of from 7 to 45 parts by weight per 100 parts of the composition.

8. A gel composition according to claim 1, wherein the ingredient (C) is a partial ester of dextrin and a fatty acid having from 8 to 20 carbon atoms.

9. A gel composition according to claim 1, wherein the ingredient (C) is used in an amount of from 7 to 25 parts by weight per 100 parts by weight of the composition.

* * * * *